United States Patent [19]

Rogoff et al.

[11] Patent Number: 4,716,039
[45] Date of Patent: Dec. 29, 1987

[54] VIRUS INSECTICIDE COMPOSITIONS

[75] Inventors: Martin H. Rogoff, Potamac, Md.; Tsuong R. Shieh, Miami, Fla.

[73] Assignee: Sandoz Pharm. Corp., E. Hanover, N.J.

[21] Appl. No.: 734,889

[22] Filed: May 16, 1985

Related U.S. Application Data

[63] Continuation of Ser. No. 638,014, Aug. 6, 1984, abandoned, which is a continuation of Ser. No. 139,845, Apr. 14, 1980, abandoned, which is a continuation of Ser. No. 4,276, Jan. 17, 1979, abandoned, which is a continuation-in-part of Ser. No. 751,725, Dec. 17, 1976, abandoned, which is a continuation-in-part of Ser. No. 596,986, Jul. 18, 1975, abandoned.

[51] Int. Cl.$^4$ ............................................. A01N 63/00
[52] U.S. Cl. ....................................................... 424/93
[58] Field of Search .......................................... 424/93

[56] References Cited

U.S. PATENT DOCUMENTS

| | | | |
|---|---|---|---|
| 3,541,203 | 11/1970 | Fogle et al. | 424/17 |
| 3,716,634 | 2/1973 | Wells | 424/93 |
| 3,743,720 | 7/1973 | Fosker et al. | 424/88 |

*Primary Examiner*—Leonard Schenkman
*Attorney, Agent, or Firm*—Gerald D. Sharkin; Richard E. Vila

[57] ABSTRACT

Virus insecticide compositions having good stability and wettability are free-flowing particles prepared by spray-drying techniques and having the virus insecticide encapsulated in a matrix comprising an intimate mixture of a protein and clay.

40 Claims, No Drawings

VIRUS INSECTICIDE COMPOSITIONS

This is a continuation of application Ser. No. 638,014, filed Aug. 6, 1984 now abandoned, which in turn is a continuation of application Ser. No. 139,845, filed Apr. 14, 1980, now abandoned, which in turn is a continuation of application Ser. No. 4,276, filed Jan. 17, 1979, now abandoned, which in turn is a continuation-in-part of application Ser. No. 751,725, filed Dec. 17, 1976, now abandoned, which in turn is a continuation-in-part of application Ser. No. 596,986, filed July 18, 1975, now abandoned.

Biological pest control has been the subject of growing interest, stimulated in no small part by the ever increasing awareness of the potentially adverse side effects of broad spectrum chemical pesticides. Biological insect control can be achieved by a variety of means. For example, competing, harmless insect populations can be reared to control a harmful insect pest. The prinicipal thrust of investigations into biological control, however, has focused on bacteria and viruses that are pathogenic for a particular pest. These insecticides can be manufactured in advance, stored in concentrated form and appled to selected areas at the most appropriate time.

Virus insecticides, and in particular those that contain proteinaceous inclusion bodies with occluded virions, have been reported for a variety of harmful insects including the cotton bollworm, the tobacco budworm, the cabbage looper, the fall armyworm, the beet armyworm, the alfalfa caterpillar and the like. Inclusion bodies with occluded virions, and the production and use of virus insecticides containing them are described, inter alia, in Steinhaus and Thompson, Preliminary Field Tests Using a Polyhedrosis Virus to Control the Alfalfa Caterpillar, Journal of Economic Entomology, vol. 42, No. 2, pp. 301–305, (April 1949); Ignoffo, Production and Virulence of a Nuclear-Polyhedrosis Virus from Larvae of *Trichoplusia ni* (Hubner) Reared on a Semi-synthetic Diet, Journal of Insect Pathology, 6, pp. 318–326 (1964); Ignoffo, the Nuclear-Polyhedrosis Virus of *Heliothis zea* (Boddie) and *Heliothis virescens* (Fabricius), Journal of Invertebrate Pathology, 7, No. 2, pp. 209–216 and 217–226 (June, 1965); Ignoffo, Possibilities of Mass-Producing Insect Pathogens, Internat. Colloq. Insect Pathol. Netherlands, pp. 91–117 (1967); Ignoffo, Viruses-Living Insecticides, Current Topics in Microbiology and Immunology, vol. 42, pp. 129–167 (1968).

Virus insecticides are manufactured in vivo by infecting and later harvesting diseased larvae, either prior to or after death. The harvested larvae may be frozen and stored for later processing or they may be processed at the time of harvest. So-called raw suspensions of the virus have been made by triturating the larvae in water and diluting the suspension so obtained. A purified virus insecticide has been obtained by triturating in the presence of water, removing exoskeleton fragments, washing with water, and freeze-drying the resulting particles. An improved method for processing the virus is disclosed in U.S. Pat. No. 3,639,578 involving contacting the insect larvae containing inclusion bodies with occluded virions with a water miscible polar organic solvent whereby the larvae are dehydrated and lipids removed from the larvae to obtain an even finer particle or a powdered mixture containing inclusion bodies with occluded virions and comminuted larvae cell matter which is dehydrated and substantially lipid-free. If desired the particles and powder produced by the prior art processes may be mixed with an extender such as lactose or the like.

Virus insecticides may be applied in the field as a dust or, as is more frequently the case, as an aqueous suspension. However, forms and methods of application which are currently available suffer from certain disadvantages. Certain of these disadvantages are related to the fact that virus insecticides, as living matter, are sensitive to many environmental or other conditions with the result that potency and effectiveness can be seriously adversely affected. For example, heat stability is always a problem with virus insecticides. Also, relatively minor amounts of the virus insecticides are required for effectiveness in field applications compared to synthetic insecticides and accordingly the preservation of the active virus for a time sufficient to come in contact with the target insect is an additional problem. More specifically, currently available application forms of the virus insecticide have been found to suffer from the disadvantage of being relatively sensitive to degradation and loss of potency due to heat and to sunlight. The ability of available forms to stick (herein called stickerability) to the plants to be protected has been also less than completely desirable with the result that quantities of the active virus can be washed by rain or otherwise removed from the plants and lost in soil before acting on the target pest. Other desired properties such as the wettability of dispersible dry formulations, e.g. compositions containing the virus insecticide and an extender such as lactose, have considerable room for improvement.

A major object of the present invention is to provide a new and improved insecticidal composition containing a virus insecticide.

Another object of the invention is to provide new and improved dispersible virus insecticide compositions having good potency and desirable physical characteristics.

Another object is to provide virus insecticide compositions which are of good potency and dispersibility and also exhibiting one or more improved physical properties such as heat stability, U.V. stability, wettability, hardness and stickerability.

A further object of the invention is to provide a method for preparing a new and improved virus insecticide composition.

These and other objectives are accomplished by the present invention in accordance with the following description thereof.

One aspect of the present invention involves the provision of particulate insecticidal compositions comprising 0.1 to 35 percent by weight of a finely divided virus insecticide secured in from 65 to 99.9 percent by weight of a matrix comprising a material selected from the group consisting of a proteinaceous material, clay and mixtures thereof.

In another aspect of the invention the particulate insecticidal compositions provided by this invention are prepared by spray drying under controlled conditions an aqueous mixture containing about 0.1 to 35 parts by weight of the virus insecticide and from about 65 to 99.9 parts by weight of a matrix material selected from the group consisting of a proteinaceous material, clay and mixtures thereof, the solids content of said aqueous mixtures based on the virus insecticide and matrix material being in the range of from 3 to 35 percent, preferably 8 to 25 percent, by weight.

The compositions provided by the invention are particulate compositions in that the compositions are composed of a multiplicity of fine particles in which the virus insecticide is secured in matrix material. The term "secured" as used herein in connection with such particles embraces an imbedding in the matrix with some portion of the insecticide exposed at the surface of the particle and also embraces a complete encapsulation of the insecticide in the matrix, the latter condition being preferred and also predominant in the particles of the invention. The particles in the composition are advantageously characterized by a fine size not exceeding 150 microns. Hence, particle size may range from as little as 3 microns up to 150 microns, and it is a further feature of the invention that satisfactory compositions having particle size of from 5 to 100, preferably 5 to 50 microns and particularly 5 to 25 microns, can be readily produced.

The particulate compositions provided by the invention, despite the exposure to heat required during spray drying, exhibit a desired amount of insecticidal potency and are generally characterized by improved resistance to potency degradation by photo-inactivation and heat denaturation. Other properties of the compositions, particularly the physical properties, will vary depending upon various factors including particularly the materials employed for the matrix. As demonstrated in the specific examples, hereinafter, compositions in which the matrix is composed only of a clay are generally characterized by good wettability but tend to have less stickerability and may, in some cases, be composed of softer particles. On the other hand, compositions in which the matrix is composed only of a vegetable protein may be generally characterized by good stickerability and hardness but tend to be less wettable. Compositions containing large amounts of animal protein tend to have good stickerability but poor wettability and hardness. Accordingly, the particularly preferred matrix materials are selected from the group consisting of vegetable protein, clay and mixtures thereof. It has also been found that compositions in which the matrix is composed of an intimate mixture of both a vegetable protein and clay have the advantage of offering good wettability, stickerability and hardness as well as other desirable properties. Accordingly, the especially preferred compositions of the invention are those in which the matrix is composed of a mixture of both a vegetable protein and clay. The ratio by weight of vegetable protein to clay may range from 0.1 to 10 parts of protein per parts by weight of clay and is preferably in the range of from 0.3 to 4 parts of vegetable protein per part of clay, more preferaly 0.5 to 3 parts by weight of clay.

The virus insecticides employed in this invention are those that contain inclusion bodies with occluded virions. Inclusion bodies have a proteinaceous, crystalline-like structure and may contain 1 to 1,000 or more occluded viral particles or virions per inclusion body. Virus diseases caused by such viruses include, inter alia, nuclear polyhedroses, cytoplasmic polyhedroses, granuloses and insect pox-viroses. About 250 viruses of this type are known for a variety of arthropod hosts such as Lepidoptera (e.g. moths and butterflies): Hymenoptera (e.g., ants, bees and wasps); Diptera (e.g. flies and mosquitoes); Orthoptera (e.g. grasshoppers); and Neuroptera (e.g. lace wings).

Preferred embodiments of this invention embrace insecticides containing a nuclear polyhedrosis virus (NPV). Nuclear polyhedrosis viruses develop in the nuclei of infected cells, are DNA viruses, and have polyhedral inclusion bodies. More specific Arthropod types in which a nuclear polyhedrosis virus has been known include Heliothis, Antographa, Pseudoplusria, Trichoplusia, Spodoptera, Tussock moth, Gypsy moth and Neodiprion. Particularly preferred embodiments of this invention embrace insecticides containing the nuclear polyhedrosis virus for the cotton bollworm (*Heliothis zea*) the tobacco budworm (*Heliothis virescens*), the cabbage looper (*Trichoplusia ni*), the fall armyworm (*Laphygma frugiperda*) and the beet armyworm (*Laphygma exigua*). Also of interest are the granuloses virus (GV) for the codling moth, fruit tree leaf roller and red-banded leaf roller. Anthropod viruses are described in more detail in Ignoffo, Viruses-Living Insecticides, Current Topics in Microbiology and Immunology, vol. 42, pp. 129-167 (1968); and Ignoffo, Possibilities of Mass-Producing Insect Pathogent, Internat. Colloq. Insect Pathol. Netherlands, pp. 99-117 (1967). Viruses readily may be obtained from scientific researchers or by simply collecting diseased larvae of a desired species in the field. Virus diseases occur naturally and any given virus is readily obtainable by field selection.

The terms "virus insecticide" and the like as used herein with reference to the insect pathogen employed in the compositions of the invention, including the amount thereof, is meant to designate not only the inclusion body itself but such other matter and debris which may not be separated from the inclusion body either by choice or the limitations of technology after treatment to free the active component from the host larvae in which it is produced. Such other matter and debris to the extent it is finely divided therefore may be employed and found in the compositions of the invention in substantial quantities without substantial adverse effect. Hence, the virus insecticide is employed in the compositions in an amount of up to 35% by weight and may contain, in addition to the inclusion bodies, substantial amounts of finely divided cell and larva matter which do not contribute to the insecticidal activity of the composition. While individual particles and the overall composition may therefore have relatively low concentrations of the pathogenic virus, it is desirable from a minimum practical standpoint that the compositions contain the active equivalent of an $LD_{50}$ of at least 1.0 microgram/ milliliter ($\gamma$/ml.). The potency of the compositions may suitably range from 0.001 $\gamma$/ml. up to 1.0 $\gamma$/ml., and is usually in the range of from 0.003 $\gamma$/ml. to 0.4 $\gamma$/ml.

Processes and methods for rearing and infection of larvae and the harvesting of the diseased larvae are well known and need not be described in detail herein. On the other hand, techniques and methods for separation and purification of the active virus component, while also well known, deserve mention as the invention also provides a distinct advantage in these areas. Hence, the acetone treated powder obtained from the process described in U.S. Pat. No. 3,639,578 may be readily used in the present invention, and it is noted that such process has the advantage of eliminating the need for the freeze-drying step in the earlier art. It is also stated in said patent that freeze-dried larvae cannot easily be processed into minus 200 mesh powders. In the present invention, and a particular advantage of a preferred embodiment thereof, the virus insecticide may be obtained without either freeze-drying or acetone. Hence, it has been found that very suitable virus insecticides are provided simply by grinding of the diseased larvae as obtained by trituration with water in the known prior art procedures, and thereafter passing through a crude filter such as a 50-150 Tyler Standard Mesh screen to remove inert cell debris. The grinding or subjection to shearing forces is essentially completed in from 1 to 20 minutes and is effected in the presence of controlled amounts of added water. Such grinding may be effected on either the diseased larvae immediately after harvesting by trituration or on the frozen and stored triturated material. The insecticide compositions of the invention will more usually contain 0.5 to 20 percent by weight of the virus insecticide, preferably 1 to 15 percent, based on the total weight of the virus insecticide and matrix material.

The compositions of the invention are prepared by spray drying an aqueous mixture of the solid composition ingredients. The spray drying may be carried out in convention spray equipment but under conditions effecting careful control of certain parameters. The aqueous mixture fed to the spray dryer is more specifically an aqueous suspension of the solid components sufficiently agitated that the solids are essentially uniformly dispersed in the water. The temperature of the aqueous feed mixture just prior to introduction into the spray dryer may range from 10° F. to 100° F., and is preferably in the range of 50° F. to 90° F. The orifice of the inlet nozzle is a major factor in determining particle size of the product and is selected accordingly. The feed mixture is introduced into the spray dryer under a pressure in the range of from 500 to 4500 psi, preferably between 1000 and 2500 psi. The spray drying which produces the compositions of the invention is essentially a rapid low temperature drying process. Inlet temperatures are accordingly regulated not to exceed 450° F. Minimum inlet temperatures may be as low as about 160° F. Usually, inlet temperatures will range from 170° F. to 360° F. and are preferably in the range of from 180° F. to 250° F. The operation of the spray dryer is conducted in such a manner that outlet temperatures (in the zone in which the resulting particles are separated from the gas) are in the range of from at least about 120° F. up to no more than 280° F., more usually in the range of from 130° F. to 220° F., and preferably in the range of from 130° F. to 200° F. The temperature drop between the inlet and outlet may vary fairly widely depending upon known factors and may as much as 220° F. The temperature difference is more usually in the range of from 40° F. to 180° F. and is preferably between 50° F. and 150° F. The heat in the spray drying is provided by a heated gas which is inert or otherwise innocuous to the virus or other ingredients in the compositions of the invention. Several conventional type heating gases may be employed, preferably air. The temperature gradients desired in the spray drying operation require that the heating gas flow be concurrent with the descending solid mass. Residence time of the solid mass in the dryer is very short and desirably does not exceed more than 3 seconds at temperatures of 160° F. or higher, usually no more than 2 seconds. Total exposure time in the process at temperatures of 120° F. or greater is preferably not more than 15 seconds, more preferably not more than 10 seconds, and recovery procedures are desirably set accordingly. When operating within the parameters described herein, it has been found that the normally heat sensitive viruses survive substantially undamaged and are secured in a dry free-flowing composition having advantages as herein described.

The feed mixture to the spray dryer is an aqueous suspension which has been sufficiently agitated that the solids are uniformly dispersed in the aqueous medium, i.e. a homogeneous suspension has been formed. The solids content of the suspension based on the virus insecticide and matrix material is in the range of from 3 to 35 percent by total weight of the aqueous suspension, preferably 8 to 25 percent by weight, and more preferably 12 to 20 percent by weight. Additional materials such as those hereinafter to be discussed may be added but the total solids content of the suspension should be in the range of from about 3 to 38 percent by total weight of the suspension, preferably 8 to 28 percent and more preferably 12 to 23 percent by weight. All solid materials in the suspension are finely divided and the matrix material and optional additives are essentially powdered materials desirably passing a 200 Tyler Standard Mesh Screen and preferably having a particle size of from 0.1 to 50 micron, preferably 0.2 to 20 microns. The virus insecticide is also finely divided. Acetone processed insecticides are powders of a very fine nature and have particle sizes in the range of from 0.5 to 100 microns, more usually from 0.5 to 20 microns. Virus insecticides not produced by the acetone process are treated by other means such as grinding in the presence of controlled amounts of water to produce a material which pass a 50-150 Tyler mesh screen, preferably 100 mesh, and in which the inclusion bodies or substance carrying the inclusion bodies are freed or reduced to a very fine size in the range of from 0.5 to 100 microns, more usually 0.5 to 25 microns, preferably 0.5 to 15 microns. Procedures for rendering virus insecticide-containing larvae into aqueous dispersions of such fineness, often called "homogenating", are well known in the art. The aqueous dispersions of the virus insecticides as produced from larvae for use in the feed to the spray dryer have a definite acidic pH typically in the range of from about pH 2.0 to 5.0, more usually a pH of from 3.0 to 5.0, and may be used as such. However, it is contemplated as preferred to adjust the pH of such dispersions to a pH in the range of from 5.5 to 8.0, preferably 6.0 to 7.5, for spray dryer purposes. In making such adjustment, it was found in independent studies that the use of a water soluble inorganic phosphate as buffering agent substantially improved the heat stability of the aqueous virus insecticide dispersions and offered definite advantages both in the dispersions fed to the spray dryer and in the solid composition produced during the drying. Accordingly, it is preferred to adjust (buffer) the pH of the aqueous dispersions fed to the spray dryer by having incorporated therein a water soluble phosphate sufficient to give a pH of from 5.5 to 8.0, preferably 6.0 to 7.5. In practice, the pH of the aqueous dispersion may be adjusted to a pH at or near the desired range using a base such as potassium hydroxide, either before, during or after the addition of the buffering agent, conveniently after buffer addition as demonstrated in Examples 2 and 3, hereinafter. Other buffering systems such as those based on acetic acid gave similar pH level but failed to provide the desired heat stability. For those systems requiring little or no adjustment as well as for those requiring substantial adjustment, a water soluble phosphate may be advantageously added in amounts of from 1 to 12 parts by weight per 100 parts by weight of the virus insecticide, preferably 3 to 9 parts per 100 parts by weight of the virus insecticide. More preferably, however, substantially greater amounts are included in the feed to the spray dryer and the product for ultimate use as demonstrated in Example 6, hereinafter. The water soluble inorganic phosphates which may be used include the alkali metal phosphate e.g., sodium and potassium phosphates, including mono- and di-hydrogen phosphates, for example, potassium phosphate, mono-hydrogen potassium phosphate and di-hydrogen potassium phosphate, preferably the latter. Hence, the inclusion of phosphate buffer in accordance with the invention benefits compositions containing a virus insecticide and a diluent such as water, inert solids and mixture thereof, the compositions having an inert solid diluent being buffered at a pH within the desired range on admixture with water.

The matrix material constitutes 65 to 99.9 percent by weight of the total weight of the virus insecticide and matrix material in the compositions of the invention, preferably 85% to 99% by weight. The clay employed in the composition may be any of the commercially available processed clays of a fine, essentially powdered, nature including, by way of illustration, Kaoline clays, Olancha clays, Attapulgus clays and Betonite clays. The preferred clays are Olancha and Attapulsites. The vegetable protein employed as matrix material may also be from any of a wide variety of sources of protein which have been processed into a fine, essentially powdered form. The materials are preferably defatted or otherwise substantially fat-free. Vegetable protein sources which may be mentioned by way of illustration include soybeans, cottonseeds, sunflower seeds and extracts of various yeasts. The preferred vegetable proteinaceous materials are soy protein and cottonseed protein, preferably those from a defatted source, more preferably defatted soybean protein. Representative of animal proteins are skim milk, casein and egg albumin. The proteinaceous material as obtained from a natural source may contain substantial amount of non-proteinaceous material and the terms "protein" and "proteinaceous material" as used herein generally contemplate materials containing as little as about at least 25% by weight of actual protein. Very suitable materials such as the preferred vegetable proteins usually contain between 40% to 75% actual protein.

The following examples illustrate the present invention.

In the following examples all spray dryings are carried out in a De Laval compact spray dryer Model 72-12.

In the following examples the following test methods are employed for the evaluation of physical characteristics:

Wettability

A Pyrex beaker (10.5×8.5 cm) No. 1000 is placed on a ring stand. One hundred ml of 30 grain hard water at 23° C. is added. A 10 cm top diameter and 1.6 cm steam inner diameter plastic funnel is placed above the beaker so that the bottom edge of the funnel stem is 10 cm above the surface of the water. A 0.5 g sample of test material is dumped into the funnel and the time required is measured for complete wetting of floating material. Wetting time of less than 60 seconds is rated as good wetting property.

Stickerability

Two drops of 0.5% solution prepared for wettability test are placed on a glass slide and allowed to dry to a thin film at room temperature for two hours. The thin film on the slide is readily visible with the naked eye. The slide is then held at a 45° angle at the distance of 10 cm beneath the faucet of tap water which is allowed to run at the rate of 100 ml per 15 seconds. The degree of wash off taking place as the result of exposing the film to a steady running water is also visible without difficulty. The material on the slide visibly washed off is recorded as "washed off" and the material visibly untouched by running water is recorded as "sticks".

Measurement of Particle Size and Particle Hardness

Approximation of diameter of particles in water suspension is measured with Petroff-Hanssen bacteria counter under phase microscope. The hardness of particles in water suspension is measured by placing the 0.5% solution into a 100 ml volumetric cylinder and inverting and righting the cylinder 30 times over 60 seconds. The integrity of particles is observed under a stereomicroscope. Soft particles usually break up to form a fine amorphous type particles, whereas hard particles remain spherical and undamaged in shape.

EXAMPLE 1

Twelve separate portions of eighty grams of acetone powder technical concentrate of *H. zea* preparation, having biological activity expressed as $LD_{50}$ of 0.003 to 0.006 $\gamma$/ml. against *H. zea* first instar, are each blended into 500 ml water with a Waring blender for one minute. Varying amounts of the additives listed in Table 1, below, are suspended in 11 liters of water and then mixed with one of the virus suspensions. The final volume of each mixture is brought to 15 liters with water and each is agitated until a homogeneous suspension is obtained. The virus suspensions are spray dried at an inlet temperature of 320° F. and an outlet temperature of 160° F. while maintaining a pressure between 2000 to 4000 psi. and using an orifice No. SA.0.0444. Each of the resulting spray dried compositions is evaluated as to potency, stickerability, wettability and particle hardness, and the results are given in Table 1, below.

TABLE 1

| Physical Characteristics of Spray Dried *H. zea* formulations | | | | | |
|---|---|---|---|---|---|
| Additives | Amount (g/15 l) | $LD_{50}$ Y/ml | Wettability | Stickerability on glass | Particle Hardness |
| 1. Olancha clay | 2320 | 0.16 | good | wash off | hard |
| 2. Kaoline | 2320 | 0.11 | good | wash off | soft |
| 3. K-Soy | 2320 | 0.14 | poor | stick | hard |
| 4. Skim milk | 2320 | 0.17 | poor | stick | amorphous |
| 5. Olancha clay & Kaoline | 1500 820 | 0.15 | good | wash off | hard |
| 6. Olancha clay & K-Soy | 1500 820 | 0.12 | good | stick | hard |
| 7. Skim milk & Kaoline | 1500 820 | N.M.* | poor | N.M.* | amorphous |
| 8. Skim milk & K-Soy | 1500 820 | N.M.* | poor | N.M.* | amorphous |
| 9. K-Soy & Olancha | 1500 820 | 0.12 | good | stick | hard |
| 10. K-Soy & Kaoline | 1500 820 | 0.10 | good | stick | hard |
| 11. Proflo | 2320 | 0.08 | poor | stick | hard |
| 12. Proflo & Kaoline | 1500 820 | 0.10 | good | stick | |

*N.M. - Not measured

The results in Table 1, above, reveal that particles comprising the virus insecticide encapsulated in a matrix comprising a vegetable protein and clay are clearly superior to similar particles prepared from either the clay or vegetable protein alone while those prepared from animal protein or mixtures of clay and animal protein are less acceptable.

EXAMPLE 2

Three separate mixtures of 800 g. of acetone powder technical concentrate of *H. zea* preparation, 50 g. of dihydrogen potassium phosphate, 2.0 g. of magnesium sulfate heptahydrate are mixed with one of the first three additives in Table 2, below, and 12 gallons of water with accompanying agitation until a homogeneous suspension is obtained. Each of the three suspensions is then brought up to a volume of 20 gallons by addition of water and adjusted to a pH of 6.5 by addition of potassium hydroxide. The suspensions are then separately spray dried as in Example 1 and the potency and physical characteristics of the resulting particle masses determined. The results are reported in Table 2, below; and compared with a standard virus insecticide identified by the Trademark Viron/H and comprising the same acetone powder technical concentrate in admixture with powdered lactose.

TABLE 2

Properties of Spray Dried *H. zea* NPV Prepared from Acetone Powder Technical Concentrate.

| Additives | g/20 gal. | Particle Size Hardness | Wetta-ability | Sticker-ability | $LD_{50}$ Y/ml |
|---|---|---|---|---|---|
| 1. Olancha clay & K-Soy | 7100 4100 | hard 5–25 microns | 45 | good | 0.12 |
| 2. Proflo | 11200 | hard 5–25 microns | 150 | good | 0.11 |
| 3. Olancha clay | 7100 4100 | hard 5–25 microns | 35 | good | 0.12 |
| 4. Viron/H | 6% tech. conc. 94% lactose powder | amorphous | 90 | poor | 0.38 |

The results in Table 2 show that the spray dried particles containing vegetable protein with or without clay have desirable potency, particle size and desirable physical characteristics.

EXAMPLE 3

Two separate mixtures of 5000 grams of frozen diseased larvae of cotton bollworm are suspended in 6 gallons of water and blended in a Waring blender for 2 minutes. The homogeneous mixtures are then screened through a 100 mesh screen to remove the insect cell debris. To the crude virus preparation, 60 g. of dihydrogen potassium phosphate, 2.0 g. of magnesium sulfate, 7.0 g. of water and the additives listed in Table 3, below, are added and final volume adjusted to 20 gallons with water. The pH is adjusted to 6.5 with potassium hydroxide. Spray drying is performed with a SA. 027 nozzle, at an inlet temperature of 200° F. an outlet temperature of 140° F. and at 1500–1800 psi. Sixty grams of spray dried powder is equivalent to the virus delivered from 40 diseased larvae. The potency and physical characterisation of the resulting particle masses are reported in Table 3, below.

TABLE 3

Properties of Spray Dried *H. zea* NPV Prepared from Frozen Diseased Larvae

| Additives | g/20 gal. | Particle Size Hardness | Wetta-ability (sec.) | Sticker-ability | $LD_{50}$ Y/ml |
|---|---|---|---|---|---|
| 1. Olancha clay | 6000 5250 | hard 5–25 microns | 35 | good | 0.103 |
| 2. Kaoline & Proflo | 6200 5000 | hard 5–25 microns | 45 | good | 0.109 |

The results in Table 3, above, show that spray dried particles encapsulating are prepared from finely divided homogenate of diseased insect larvae in accordance with the invention provide satisfactory and desired properties.

EXAMPLE 4

Spray dried particle masses obtained in Examples 2 and 3 are suspended into an aliquot of water and placed into a petri dish. The virus suspension are then exposed to ultra-violet irradiation for 5 seconds and residual insecticidal activity measured. The results are shown in Table 4.

TABLE 4

Effect of UV-irradiation on Insecticidal Activity of Various Preparation

| Virus Formulations | $LD_{50}$ Control | $LD_{50}$ UV irradiation | Residual Activity |
|---|---|---|---|
| 1. Viron/H (standard | 0.25 | 0.62 | 40 |
| 2. Tech. conc. & clay & K-Soy | 0.12 | 0.20 | 60 |
| 3. Tech. conc. & Proflo | 0.14 | 0.17 | 82 |
| 4. Tech. conc. & clay & Proflo | 0.11 | 0.20 | 55 |
| 5. Frozen larvae & clay & K-Soy | 0.11 | 0.15 | 74 |
| 6. Frozen larvae & Kaoline & Proflo | 0.13 | 0.15 | 87 |

The results in Table 4 show that spray dried virus preparations having a protective encapsulation matrix have improved protection against ultra-violet irradiation.

EXAMPLE 5

Spray dried preparations obtained in experiments 2 and 3 stored at 50° C. and 38° C. for periods of time and residual potency determined as reported in Table 5, below:

TABLE 5

|  | Half Life | |
|---|---|---|
|  | 50° C. (days) | 38° C. (weeks) |
| 1. Viron/H | 2 | 1 |
| 2. Tech. conc. & clay & K-Soy | 8 | 6.0 |
| 3. Tech. conc. & Proflo | 12 | 9.5 |
| 4. Tech. conc. & clay & Proflo | 8 | 2.5 |
| 5. Frozen larvae & clay & K-Soy | 10 | 5.5 |
| 6. Frozen larvae & Kaoline & Proflo | 9 | 4.0 |

The results in Table 5 demonstrate that spray dried particles obtained by the present invention show significant improvement in half life of the virus infectivity against *H. zea*.

EXAMPLE 6

Two additional compositions of the invention (Formulations I and II) are composed as follows:

| A. Formulation I (Protein matrix with no clay) | |
|---|---|
| 1. In Feed to Spray Drier: | |
| *Heliothis zea* virus | 19.2 grams |
| K-SOY | 21.54 grams |
| KH$_2$PO$_4$ | 1.44 grams |
| Total | 42.18 grams |
| Total Dry Solids basis | 27.0 grams |
| 2. Final Product after Dilution of Spray Dried Product in Ribbon Blender with K-SOY and Silica Dioxide (HI-SIL) | |
| *Heliothis zea* virus | 19.2 grams |
| K-SOY | 51.54 grams |
| KH$_2$PO$_4$ | 1.44 grams |
| HI-SIL | 3.0 grams |
| B. Formulation II (Protein and clay matrix) | |
| *Heliothis zea* Virus | 20.6 grams |
| K-SOY | 35.08 grams |
| ATTACLAY | 17.24 grams |
| KH$_2$PO$_4$ | 3.56 grams |

Formulations I and II are prepared by spray drying in commercial size apparatus generally in accordance with the procedure of Example 3, above, at an inlet temperature of about 320° F. and an outlet temperature of about 160° F. for formulation I and inlet temperature of 260° F. and outlet temperature of 140° F. for formulation II. The *Heliothis zea* virus in the above formulations represents the total amount of a concentrated aqueous virus cream prepared by the charging of 20 parts of frozen diseased *Heliothis zea* larvae along with 80 parts of water to a grinder and grinding for about 1-2 minutes after which about 0.25 parts of dihydrogen potassium phosphate is added along with sufficient potassium hydroxide to obtain a pH of pH 6.5, after which grinding is continued for 1-2 minutes, the resulting suspension filtered through a 100 mesh screen to remove larger cell debris, the screened liquid suspension then centifuged and the supernatant liquid above the resulting creamy mass removed to obtain the virus cream having a water content of about 75-80% by weight. The dihydrogen potassium phosphate in each of the above formulations represents an amount separately added to the aqueous dispersions fed to the spray dryer and hence is in addition to residual dihydrogen potassium phosphate contained in the virus cream. Initial potency of the product formulations I and II is between 0.1 and 0.2 γ/ml and both such formulations exhibit a half life at 50° C. of greater than 10 days, as well as good overall properties for combatting Heliothis larvae in cotton plants.

In the foregoing Examples, Proflo is a tradename for a defatted cottonseed powder and K-Soy is a tradename for a defatted soybean powder. The Kaoline is Georgia Kaoline.

The measurement of insecticidal activity or potency as used and referred to in this specification is based on determination of the LD$_{50}$ value reported in micrograms per ml. (γ/ml.) of diet required to provide a level dose for 50 percent of the first instar larvae grown at a temperature of 30° C. The method is basically described in Insect Pathology; 6, 737–45 (1965) in connection with *Trichopusia ni* NPV potency estimation. The nutrient employed in such test has the following composition:

| Ingredient: | | Amount |
|---|---|---|
| Distilled water | ml | 3,100 |
| Methyl parahydroxybenzoate (15% w./v. in 95% ethyl alcohol) | ml | 36 |
| Choline chloride (0.1 g./ml. water) | ml | 36 |
| Potassium hydroxide, 4 molar | ml | 18 |
| Formalin (0.1 g./ml.) | ml | 15 |
| Vitamin stock[1] | ml | 6 |
| Casein | g | 126 |
| Sucrose | g | 126 |
| Wheat germ | g | 108 |
| Agar | g | 90 |
| Wesson's salts | g | 36 |
| Alphacel | g | 18 |
| Ascorbic acid | g | 15 |
| Antibiotic (chlortetracycline, kanamycin) | | |

[1]600 mg. niacin, 600 mg. calcium pantothenate, 300 mg. riboflavin, 150 mg. each of thiamin, pyridoxin and folic acid, 12 mg. biotin, and 1.2 mg. of vitamin B-12 in 100 ml. distilled water.

Preparation of nutrient is described in Journal of Invertebrate Pathology, 7, No. 2, pp. 217–226 (June 1965).

What is claimed is:

1. A particulate insecticidal composition comprising a free-flowing particle mass containing 0.1 to 35 percent by weight of a finely divided virus insecticide in which virions are in inclusion body form secured in from 65 to 99.9 percent by weight of a matrix comprising a material selected from the group consisting of a normally solid defatted vegetable proteinaceous material and mixtures of normally solid defatted vegetable proteinaceous material and clay in a weight ratio of 0.1 to 10 parts of said proteinaceous material per part of clay, such particles having a size in the range of from 3 to 150 microns, said virus insecticide being free of viruses which are not in inclusion body form.

2. A particulate insecticidal composition of claim 1 comprising a free-flowing particle mass containing 0.1 to 35 percent by weight of a finely divided virus insecticide secured in from 65 to 99.9 percent by weight of a matrix comprising a material selected from the group consisting of defatted soybean powder, defatted cottonseed powder, mixtures of defatted soybean powder and clay in a weight ratio of 0.1 to 10 parts of soybean powder per part of clay and mixtures of defatted cottonseed powder with clay in a weight ratio of 0.1 to 10 parts of cottonseed powder per part of clay, such particles having a size in the range of from 3 to 150 microns.

3. The composition of claim 2 in which the matrix material is defatted soybean powder.

4. The composition of claim 2 in which the matrix material is a mixture of defatted soybean powder and clay in a weight ratio of 0.3 to 4 parts of defatted soybean powder per part of clay.

5. The composition of claim 2 in which the virus insecticide is *Heliothis zea*, NPV.

6. The composition of claim 2 in which the particles contain a water soluble inorganic phosphate whereby the particle mass provides an aqueous mixture buffered at a pH of from 6 to 7.5 on admixture of the particle mass with water.

7. The composition of claim 6 in which the phosphate is dihydrogen potassium phosphate.

8. The composition of claim 6 in which the virus insecticide is *Heliothis zea*, NPV.

9. The composition of claim 8 in which the matrix material is defatted soybean powder.

10. The composition of claim 9 in which the phosphate is dihydrogen potassium phosphate.

11. A particulate virus insecticide composition produced by atomizing an aqueous dispersion having a total solids content of from 3 to 35 percent by weight and containing 0.1 to 35 parts by dry weight of a virus insecticide in which virions are in inclusion body form and correspondingly 65 to 99.9 parts by weight of a finely divided matrix material selected from the group consisting of a normally solid defatted vegetable proteinaceous material and mixtures thereof with clay in a weight ratio of 0.1 to 10 parts of said proteinaceous material per part of clay, into a cocurrent flow of heated gas having an inlet temperature of from 160° F. to 450° C. in the zone of atomization and separating the resulting particles from the gas in an outlet zone in which the gas outlet temperature is from 120° F. to 280° F., the time of exposure of the solid mass to temperatures of at least 160° F. not exceeding 3 seconds, the separated resulting particles constituting a free flowing particle mass containing 0.1 to 35 percent by weight of finely divided virus insecticide secured in from 65 to 99.9 percent by weight of the matrix material, and the particles having a size in the range of from 3 to 150 microns, said virus insecticide being free of viruses which are not in inclusion body form.

12. The composition of claim 11 in which the aqueous dispersion is atomized at a pressure of from 500 to 4500 psi.

13. The composition of claim 11 in which the outlet temperature is in the range of from 130° F. to 200° F.

14. The composition of claim 11 in which the inlet temperature is from 170° F. to 360° F. and the outlet temperature is from 130° F. to 220° F.

15. The composition of claim 14 in which the virus insecticide is present in the dispersion in the amount of from 0.5 to 20 parts by dry weight and in which the resulting particles have a size in the range of from 5 to 100 microns.

16. The composition of claim 15 in which the matrix material is a mixture of vegetable protein and clay in a weight ratio of 0.1 to 10 parts of protein per part of clay.

17. The composition of claim 11 in which the matrix material is defatted vegetable protein.

18. The composition of claim 17 in which the outlet temperature is in the range of from 130° F. to 200° F.

19. The composition of claim 18 in which the virus insecticide is *Heliothis zea*, NPV.

20. The composition of claim 17 in which the virus insecticide is *Heliothis zea*, NPV.

21. The composition of claim 11 in which the dispersion contains a water soluble inorganic phosphate whereby said dispersion is buffered at a pH of from 6.0 to 7.5.

22. The composition of claim 21 in which the matrix material is defatted vegetable protein.

23. The composition of claim 22 in which the outlet temperature is in the range of from 130° F. to 200° F.

24. The composition of claim 23 in which the virus insecticide is *Heliothis zea*, NPV.

25. The composition of claim 24 in which the dispersion is buffered at the pH of from 6 to 7.5 with dihydrogen potassium phosphate.

26. The composition of claim 25 in which the vegetable protein is defatted soybean powder.

27. The composition of claim 21 in which the matrix material is a mixture of vegetable protein and clay in a weight ratio of 0.1 to 10 parts of protein per part of clay.

28. The method of preparing a particulate virus insecticide composition comprising atomizing an aqueous dispersion containing 0.1 to 35 parts by dry weight of a virus insecticide in which virions are in inclusion body form and correspondingly 65 to 99.9 parts by dry weight of a finely divided matrix material selected from the group consisting of a normally solid defatted vegetable proteinaceous material and mixtures thereof with clay in a weight ratio of 0.1 to 10 parts of said proteinaceous material per part of clay, the solids content of said dispersion based on the virus insecticide and matrix material being in the range of from 3 to 35 percent by total weight of the aqueous dispersion, into a cocurrent flow of heated gas having an inlet temperature of from 160° F. to 450° F. in the zone of atomization and separating the resulting particles from the gas in an outlet zone in which the gas outlet temperature is from 120° F. to 280° F., the time of exposure of the solid mass to temperatures of at least 160° F. not exceeding 3 seconds, said virus insecticide being free of viruses which are not in inclusion body form.

29. The method of claim 28 in which the aqueous dispersion is atomized at a pressure of from 500 to 4500 psi.

30. The method of claim 28 in which the outlet temperature is in the range of from 130° F. to 200° F.

31. The method of claim 28 in which the inlet temperature is from 170° F. to 360° F. and the outlet temperature is from 130° F. to 220° F.

32. The method of claim 31 in which the virus insecticide is present in the dispersion in the amount of from 0.5 to 20 parts by dry weight and in which the resulting particles have a size in the range of from 5 to 100 microns.

33. The method of claim 28 in which the matrix material is defatted vegetable protein.

34. The method of claim 33 in which the virus insecticide is *Heliothis zea*, NPV.

35. The method of claim 34 in which the outlet temperature is in the range of from 130° F. to 200° F.

36. The method of claim 28 in which the dispersion contains a water soluble inorganic phosphate whereby said dispersion is buffered at a pH of from 6.0 to 7.5.

37. The method of claim 36 in which the matrix material is defatted vegetable protein and the virus insecticide is *Heliothis zea*, NPV.

38. The method of claim 37 in which the outlet temperature is in the range of from 130° F. to 200° F.

39. The method of claim 38 in which the phosphate is dihydrogen sodium phosphate.

40. The method of claim 36 in which the matrix material is a mixture of vegetable protein and clay in a weight ratio of 0.3 to 4 parts of protein per part of clay and the virus insecticide is *Heliothis zea*, NPV.

* * * * *